(12) United States Patent
Murakami et al.

(10) Patent No.: US 7,264,618 B2
(45) Date of Patent: Sep. 4, 2007

(54) ULTRASONIC TREATMENT APPARATUS

(75) Inventors: Eiji Murakami, Tokyo (JP); Ryoji Masubuchi, Aomori (JP)

(73) Assignee: Olympus Corporation, Tokyo (JP)

( * ) Notice: Subject to any disclaimer, the term of this patent is extended or adjusted under 35 U.S.C. 154(b) by 287 days.

(21) Appl. No.: 10/815,424

(22) Filed: Apr. 1, 2004

(65) Prior Publication Data

US 2004/0186463 A1    Sep. 23, 2004

(51) Int. Cl.
  *A61B 18/18*   (2006.01)
  *A61B 17/32*   (2006.01)
(52) U.S. Cl. .................... 606/27; 606/169; 606/45
(58) Field of Classification Search .............. 606/1, 606/27, 28, 41, 45, 49, 169; 604/22
See application file for complete search history.

(56) References Cited

U.S. PATENT DOCUMENTS 6,066,151 A    5/2000 Miyawaki et al.
6,193,709 B1 *  2/2001 Miyawaki et al. .......... 606/1
6,214,023 B1 *  4/2001 Whipple et al. .......... 606/169
6,425,907 B1 *  7/2002 Shibata et al. .......... 606/169

FOREIGN PATENT DOCUMENTS

| JP | 11-113918 | 4/1999 |
| JP | 2000-254138 | 9/2000 |
| JP | 2000-296135 | 10/2000 |
| JP | 2002-119518 | 4/2002 |

* cited by examiner

*Primary Examiner*—Michael Peffley
(74) *Attorney, Agent, or Firm*—Scully, Scott, Murphy & Presser, P.C.

(57) ABSTRACT

An ultrasonic treatment apparatus of the invention is provided with an improved cleaning ability and easy recyclability. A grasping member (1720) includes a first element (1721) molded of a heat resistant resin, and a second element (1722) located inside the first element (1721) as a reinforcement in such a manner that the first element (1721) covers the outer surface of the second element (1722) entirely.

6 Claims, 12 Drawing Sheets

ULTRASONIC TREATMENT APPARATUS

TECHNICAL FIELD

The present invention relates to a technology for performing medical procedures such as cutting, removing, and coagulation of living tissues using ultrasonic vibration.

BACKGROUND ART

An example of an ultrasonic treatment apparatus for performing medical procedures such as cutting, removing, and coagulation of a living tissue using ultrasonic is disclosed in U.S. Pat. No. 6,193,709. The ultrasonic treatment apparatus includes an elongated insertion sheath that is inserted into a hollow portion of a body, a probe that is projected from a distal end of the insertion sheath, and a tip action unit that is rotatably arranged at the distal end of the insertion sheath and that moves in an opening/closing manner with respect to the probe. An operating section is provided near the proximal end of the ultrasonic treatment apparatus to operate the tip action unit rotationally.

In such type of ultrasonic treatment apparatus, operation of the operating section moves the tip action unit closer to the probe to grasp the living tissue between the probe and the tip action unit. In addition, by transmitting the ultrasonic vibration to the probe, it is possible to perform the medical procedures such as coagulation and cutting of the living tissue between the probe and the tip action unit.

The tip action unit of the ultrasonic treatment apparatus includes a jaw that moves in an opening/closing manner in response to the operation of the operating section, and a grasping member pivotably supported by the jaw. This configuration is effective to apply a uniform grasping force over the entire length of the grasping member when the tip action unit is closed to grasp the living tissue between the probe and the tip action unit. Specifically, the grasping member is rotatably attached to the jaw via a pin that is arranged perpendicular to the longitudinal direction of the probe. In this case, when grasping the living tissue, the grasping member is forced to tilt to follow the deflection of the probe and thus applying a uniform grasping force over the entire length of the grasping member.

The grasping member includes two elements: a first element and a second element. The first element is molded of a resin that exhibits a low friction coefficient against the probe and has excellent heat resistance and abrasion resistance, such as polytetrafluoroethylene (PTFE). It is arranged in a direction facing the probe. The second element is molded of a metal in a frame shape, which has a relatively high rigidity and tenacity, and is configured to cover the outer surface of the first element and contains a portion for pivotably supporting the jaw.

Conventionally, such the ultrasonic treatment apparatus is discarded to be replaced with a new one after completion of every surgical operation. In consideration of recent global environmental problems, however, the need for recycling the ultrasonic treatment apparatus is gradually increasing. Even if the ultrasonic treatment apparatus is once used in the surgical operation, if it can be cleaned sufficiently, it will be applied to a next surgical operation without any trouble to contribute to reduction of environment burden and operational costs.

In the conventional ultrasonic treatment apparatus, contaminants such as blood are attached to the insertion sheath to be inserted into the hollow portion of the body and the tip action unit. Therefore, it is extremely important to clean the components easily and sufficiently before recycling the apparatus. Particularly, in the tip action unit that consists of a plurality of elements, contaminants such as blood entering into spacing between the first element and the second element require a very long time to be cleaned.

The present invention is to solve the above problems and accordingly provides an ultrasonic treatment apparatus that can achieve an improved cleaning mechanism for cleaning in a shorter time and an easy recyclability.

An ultrasonic treatment apparatus for performing a medical treatment to a living tissue, according to one aspect of the present invention includes a probe to which ultrasonic vibration is applied, and a tip action unit that moves in an opening/closing manner with respect to the probe on operation of an operating section. The tip action unit includes a jaw that moves in an opening/closing manner in response to the operation of the operating section, and a grasping member pivotably supported by the jaw for grasping the living tissue with the probe. The grasping member includes a first element molded of a heat resistant resin, and a second element located inside the first element as a reinforcement in such a manner that the first element covers the outer surface of the second element entirely. The ultrasonic vibration is applied to the probe while grasping the living tissue between the probe and the tip action unit.

An ultrasonic treatment apparatus for performing a medical treatment to a living tissue, according to another aspect of the present invention includes a probe to which ultrasonic vibration is applied, and a tip action unit that moves in an opening/closing manner with respect to the probe on operation of an operating section. The tip action unit includes a jaw that moves in an opening/closing manner in response to the operation of the operating section, and a grasping member pivotably supported by the jaw for grasping the living tissue with the probe. The grasping member includes at least a first element molded of a heat resistant resin, and a second element located inside the first element as a reinforcement in such a manner that the first element covers the outer surface of the second element with at least a portion of the second element exposed. The ultrasonic vibration is applied to the probe while grasping the living tissue between the probe and the tip action unit.

An ultrasonic treatment apparatus according to still another aspect of the present invention has a mechanism that a filling member is filled between the first element and the second element to tightly contact the first element with the second element.

An ultrasonic treatment apparatus according still another aspect of the present invention has a mechanism that the second element is a metallic material extended along an extending direction of the probe.

An ultrasonic treatment apparatus according to still another aspect of the present invention has a mechanism that the second element includes a portion pivotably supported by the jaw.

An ultrasonic treatment apparatus for performing a medical treatment to a living tissue, according to still another aspect of the present invention includes a probe to which ultrasonic vibration is applied, and a tip action unit that moves in an opening/closing manner with respect to the probe on operation of an operating section. The tip action unit includes a jaw that moves in an opening/closing manner in response to the operation of the operating section, and a grasping member pivotably supported by the jaw for grasping the living tissue with the probe. The grasping member is molded of a heat resistant resin. The ultrasonic vibration is applied to the probe while grasping the living tissue between the probe and the tip action unit.

BEST MODE FOR CARRYING OUT THE INVENTION

Exemplary embodiments of an ultrasonic treatment apparatus according to the present invention are described below in detail with reference to the accompanying drawings.

First Embodiment

Figure 1:
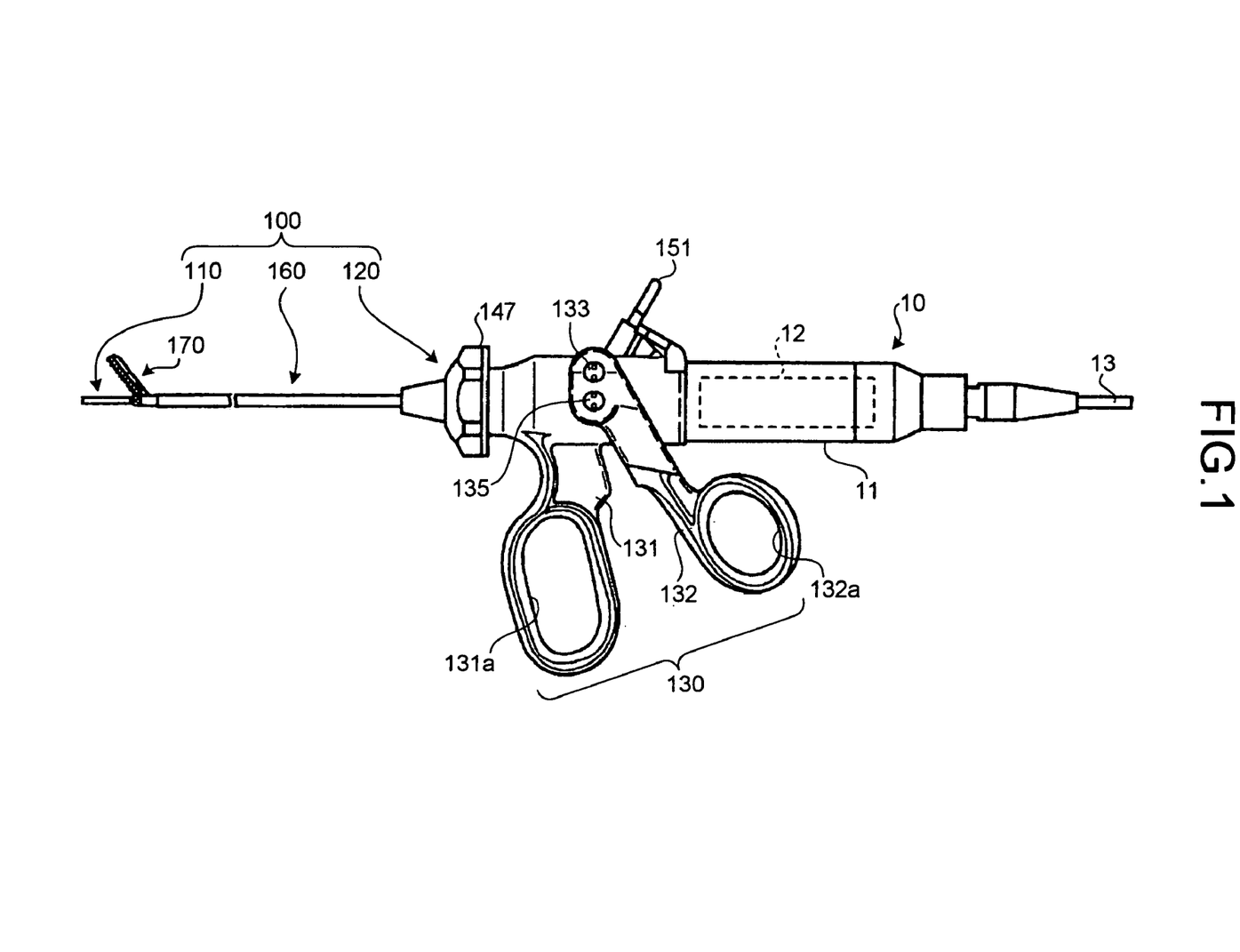
FIG. 1 is an external view of an ultrasonic treatment apparatus according to a first embodiment of the present invention.

FIG. 1 to FIG. 9 are schematic diagrams for illustrating an ultrasonic treatment apparatus according to a first embodiment of the present invention. The ultrasonic treatment apparatus is employed for performing medical procedures such as cutting, removing, and coagulation of living tissues using ultrasonic wave. The ultrasonic treatment apparatus includes a vibrator 10 and a treatment unit 100 separable from each other as illustrated in FIG. 1.

The vibrator 10 includes, inside a vibrator cover 11, an ultrasonic vibrator 12 as a vibrating source. The ultrasonic vibrator 12 such as a piezoelectric element converts a given electric signal into a mechanical vibration. The ultrasonic vibrator 12 may vibrate at a frequency of 20 kilohertz or higher. The first embodiment applies one that vibrates at 47 kilohertz when the electric signal is given.

Figure 5:
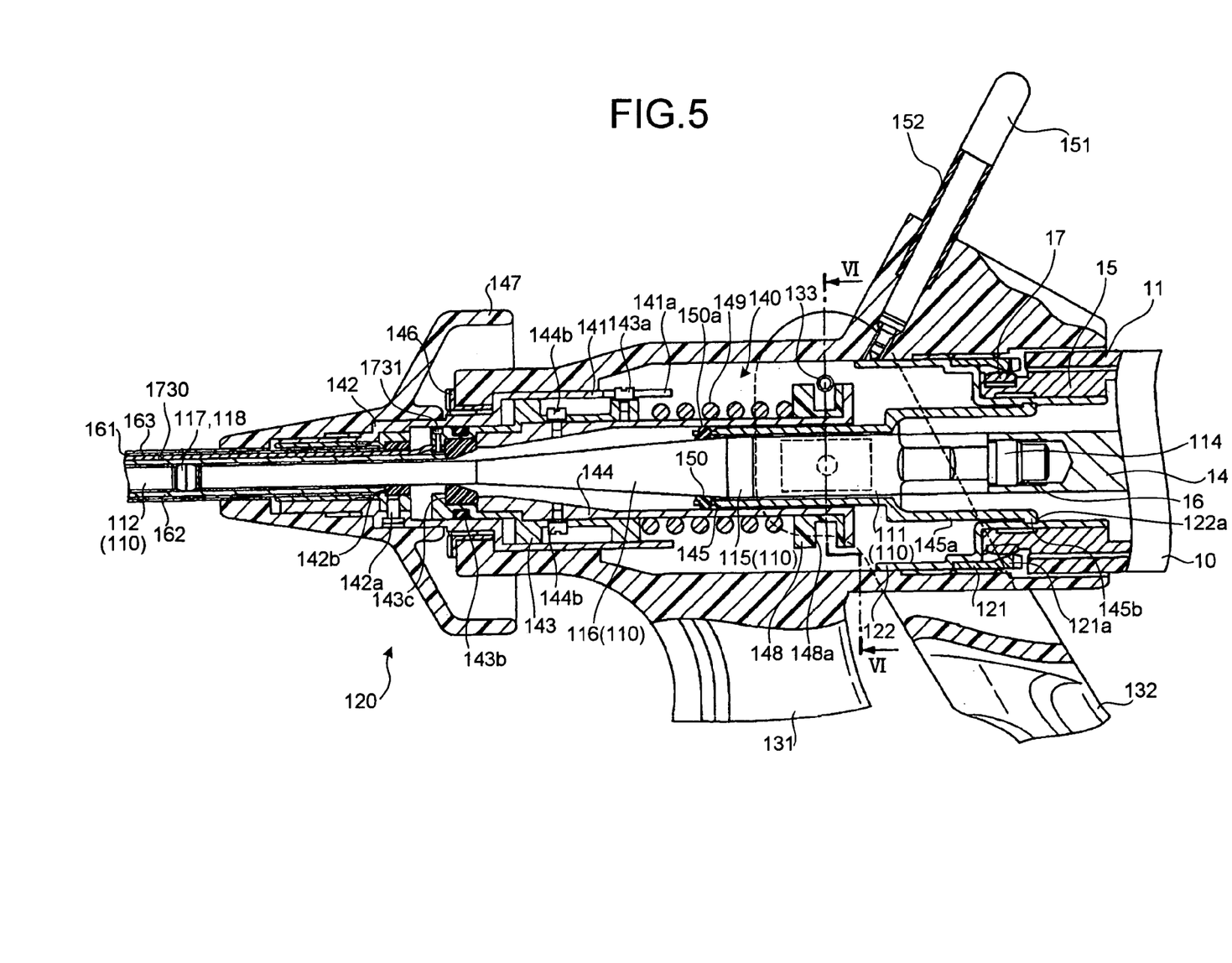
FIG. 5 is a cross-sectional side view of the ultrasonic treatment apparatus illustrated in FIG. 1.

As illustrated in FIG. 1 and FIG. 5, a cable 13 is connected to the rear end of the vibrator 10 (on the right side end of the vibrator 10 in FIG. 1). On the other hand, a horn 14 and an attachment 15 are provided at the front end of the vibrator 10 (on the left side end of the vibrator 10 in FIG. 5). The cable 13 is employed to lead an electric signal output from a power source (not shown) to the ultrasonic vibrator 12 to vibrate it. The horn 14 is attached to the ultrasonic vibrator 12 to amplify and output the vibration when the ultrasonic vibrator 12 vibrates. A female threaded portion 16 is formed in the distal end of the horn 14. The attachment 15 is employed to detachably connect the vibrator 10 to the treatment unit 100 later described, and includes an attachment ring 17 around the perimeter of the distal end. The attachment ring 17 is a metallic annular member, which is partly cut off for being elastically deformable in the radial direction though it is not illustrated definitely in the drawing.

The treatment unit 100 includes a probe 110, and a unit body 120 configured to attach the probe 110 exteriorly.

The probe 110 is an elongated member having an input portion 111, a waveguide portion 112 and a treatment portion 113. A male threaded portion 114 is formed around the proximal end of the input portion 111. When the male threaded portion 114 is mated with the female threaded portion 16 of the horn 14, the probe 110 is detachably attached to the horn 14 of the vibrator 10. The probe 110 is composed of a bio-compatible metallic material such as a titanium alloy. The length of the probe 110 is formed as a length corresponding to an integral multiple of a half wavelength of the vibration caused by the ultrasonic vibrator 12. When the ultrasonic vibrator 12 vibrates, the vibration amplified through the horn 14 is transmitted to the probe 110, which resonates with the vibrator to ultrasonic-vibrate the treatment portion 113.

The input portion 111 of the probe 110 is formed in a cylindrical shape with a relatively large diameter having a flange 115 at the distal end thereof as illustrated in FIG. 7(a). The flange 115 is a large diameter portion formed around the perimeter at a position that corresponds to a segment of vibration closest to the proximal end when the ultrasonic vibrator 12 vibrates. The flange 115 has flat portions 115a formed on a plurality of positions in the outer circumferential surface thereof as illustrated in FIG. 7(b).

The waveguide portion 112 of the probe 110 is an elongated columnar member formed to have a smaller diameter than that of the input portion 111 as illustrated in FIG. 7(a), and is connected to the distal end of the input portion 111 via a tapered portion 116. The waveguide portion 112 has small diameter portions 117 formed on a plurality of positions that correspond to segments of vibration when the ultrasonic vibrator 12 vibrates. In addition, rubber rings 118 are mounted around a plurality of positions that correspond to segments of vibration. The small diameter portions 117 have a reduced cross section so as to provide the treatment portion 113 with a desired amplitude when the ultrasonic vibrator 12 vibrates. The rubber rings 118 are interposed between the waveguide portion 112 and an insert portion 160 later described to prevent the waveguide portion 112 and the insert portion 160 from interfering with each other.

The treatment portion 113 of the probe 110 is a portion that directly contacts living tissues such as blood vessels, and has a uniform outer diameter and is formed in a linearly extending cylindrical shape with a small diameter.

As illustrated in FIG. 1 and FIG. 5, the unit body 120 is formed in a cylindrical shape having openings at both ends. The unit body 120 includes an external connection member 121 and an internal connection member 122 arranged on the inner circumference in the opening at the proximal end, and also includes an operating section 130 arranged on the outer circumference in the middle portion.

The external connection member 121 and the internal connection member 122 are attached to the unit body 120 to form an annular groove therebetween for accommodating the attachment 15 and the attachment ring 17 of the vibrator 10 therein. The external connection member 121 has a projection 121a on the inner circumferential surface at the proximal end thereof. The projection 121a has such an inner diameter that restricts the passage of the attachment ring 17 when it is in a normal state and allows the passage of the attachment ring 17 when it has a reduced diameter due to elastic deformation.

When the attachment 15 and the attachment ring 17 of the vibrator 10 are squeezed in between the external connection member 121 and the internal connection member 122, the attachment ring 17 is appropriately elastically deformed and engaged with the projection 121a. As a result, the vibrator 10 can be detachably attached to the proximal end of the unit body 120.

Figure 6:
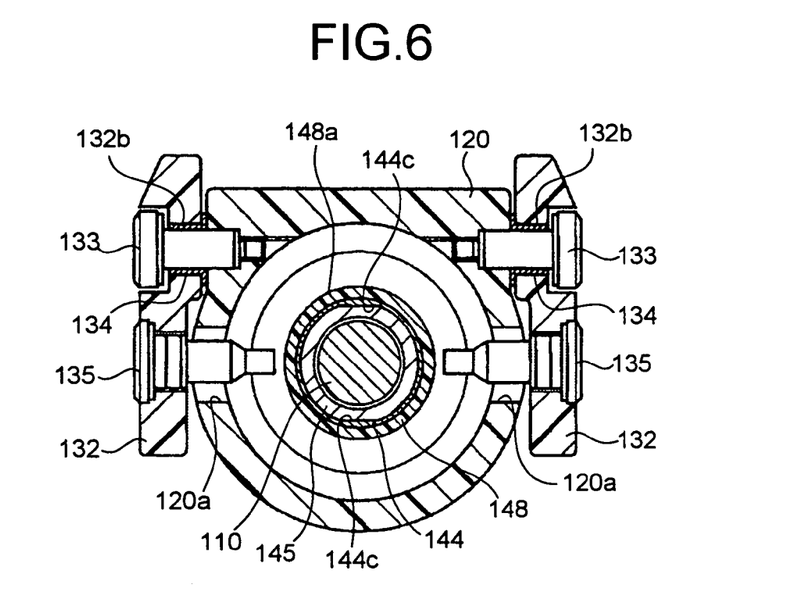
FIG. 6 is a cross-sectional view cut along VI-VI line in FIG. 5.
Figure 7:
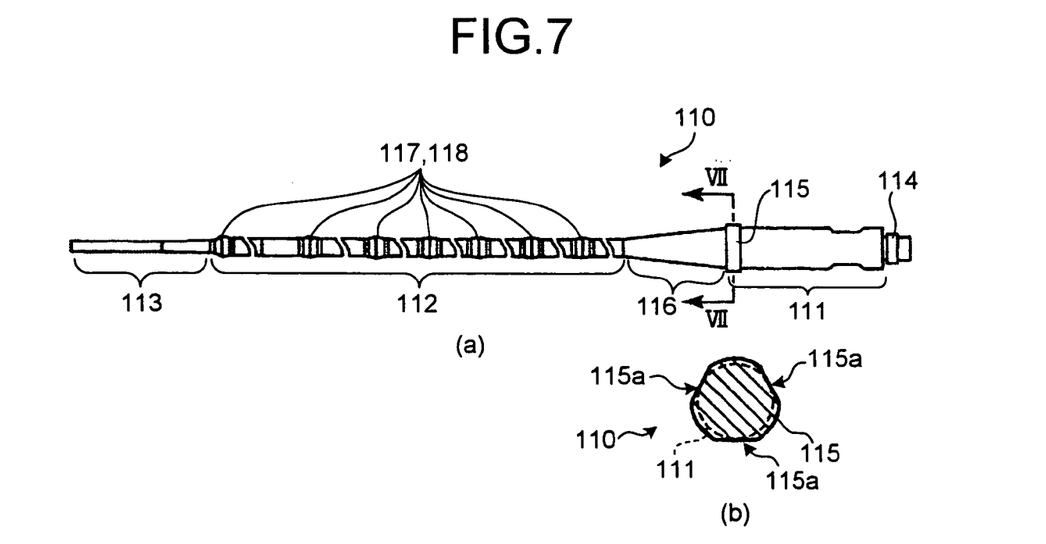
FIG. 7(a) is an external side view of a probe of the ultrasonic treatment apparatus illustrated in FIG. 1.
FIG. 7(b) is a cross-sectional view cut along VII-VII line in FIG. 7(a)
Figure 8:
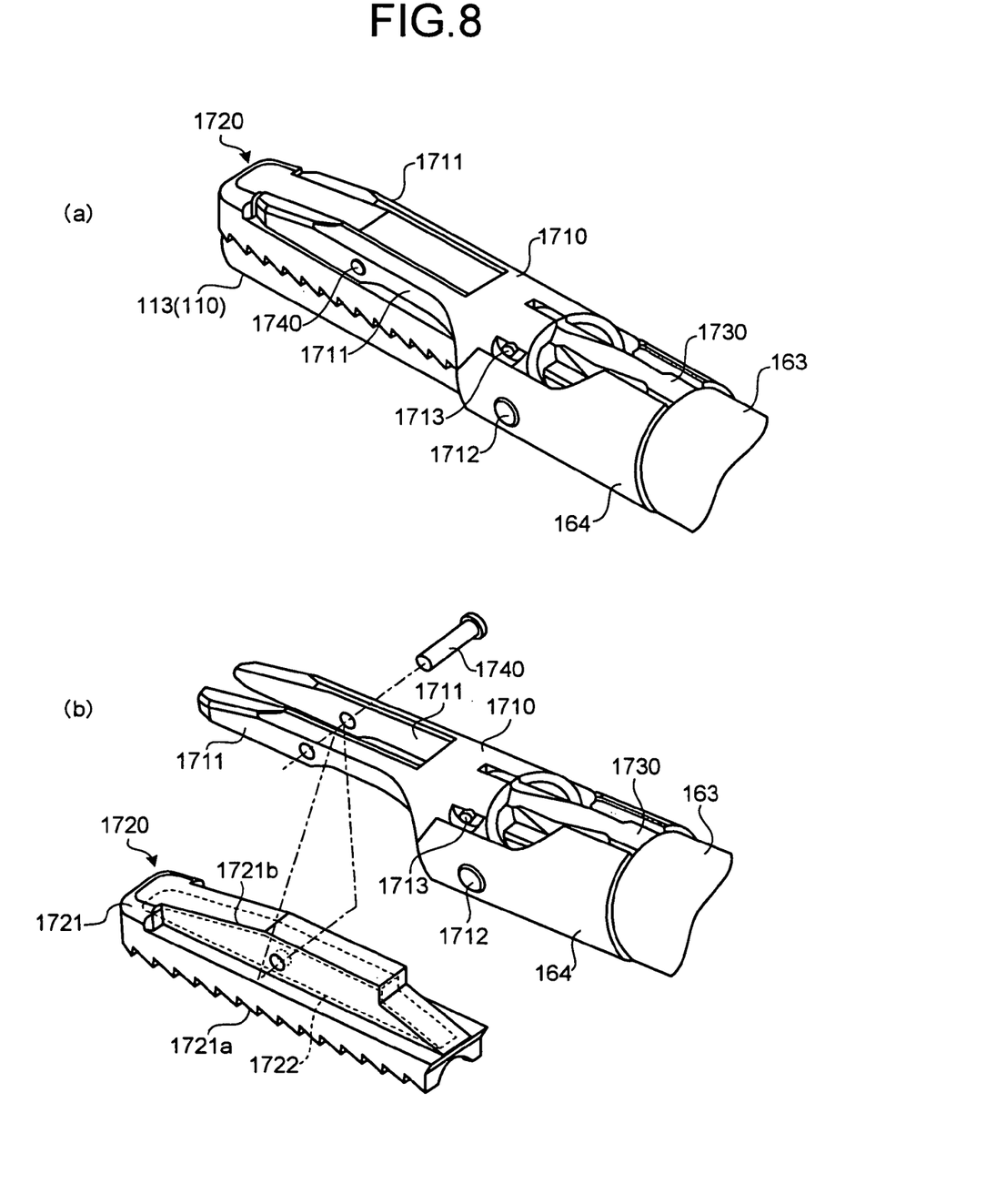
FIG. 8(a) is a perspective view of a tip action unit.
FIG. 8(b) is an exploded perspective view of the tip action unit.
Figure 9:
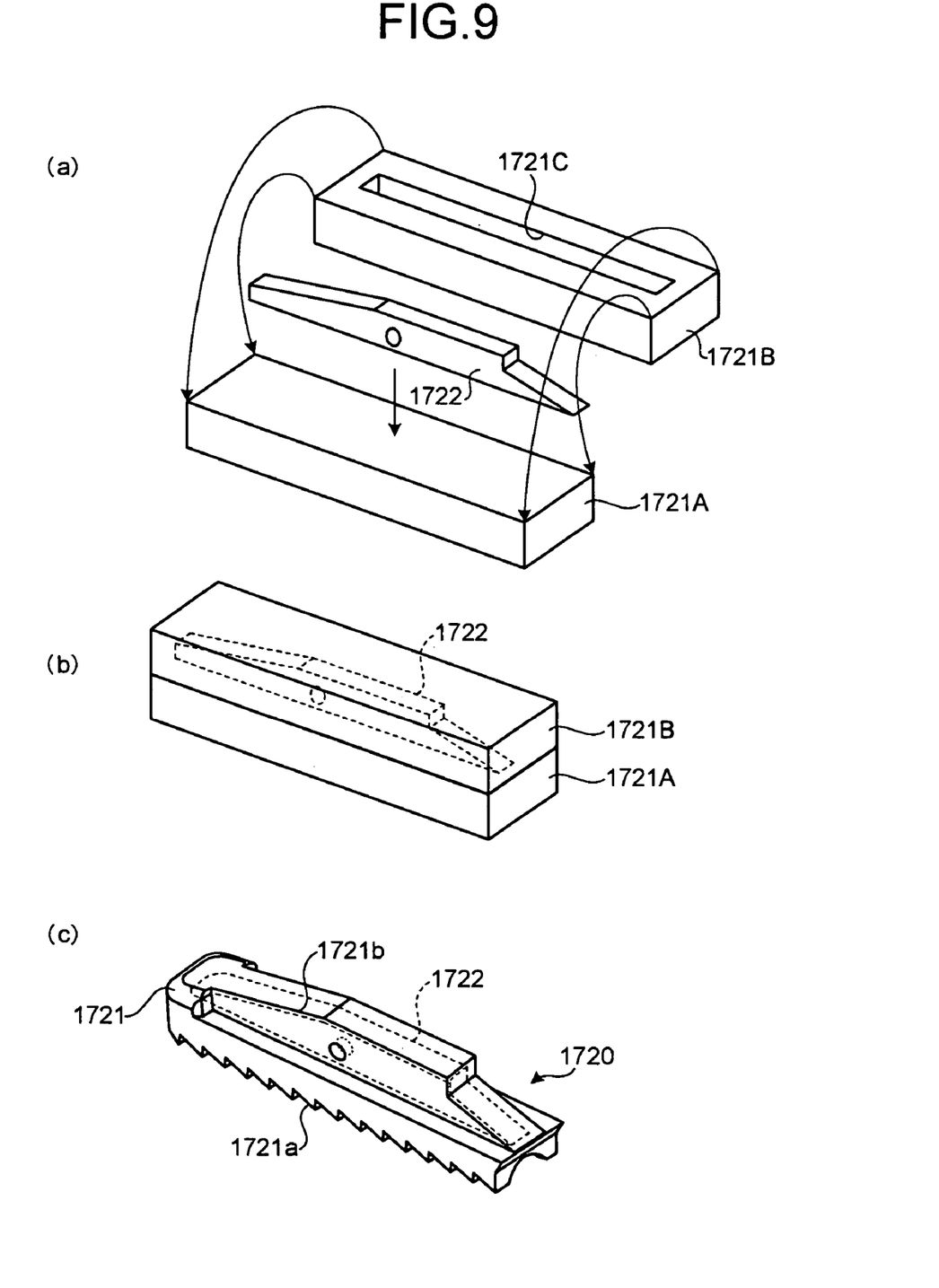
FIG. 9(a) to FIG. 9(c) are schematic diagrams for illustrating process steps of manufacturing a grasping member.

As illustrated in FIG. 1, FIG. 5, and FIG. 6, the operating section 130 is a portion to be operated by an operator for treatment of living tissues, and includes a stationary handle 131 and a movable handle 132.

The stationary handle 131 extends from the unit body 120 outward in the radial direction and has a stationary finger-engaging portion 131a at the extended end thereof. The stationary handle 131 is formed integrally with the unit body 120. The movable handle 132 has a movable finger-engaging portion 132a at the proximal end thereof, and has pin insertion holes 132b at the bifurcated distal ends thereof. The movable handle 132 is rotatably attached to the unit body 120 using fulcrum pins 133 mounted to the unit body 120 through the pin insertion holes 132b. As illustrated in FIG. 6, bushes 134 composed of a resin having a low friction coefficient such as PTFE are disposed around the perimeters of the fulcrum pins 133 for the purpose of providing an improved sliding ability relative to the movable handle 132. The movable handle 132 includes action pins 135 arranged at locations closer to the proximal ends than the fulcrum pins 133. These action pins 135 have individual distal ends that are protruded inside the unit body 120 through action grooves 120a formed in the unit body 120.

In the operating section 130 equipped with the stationary handle 131 and the movable handle 132, when fingers are engaged in the stationary finger-engaging portion 131a and the movable finger-engaging portion 132a and operated to open/close, the movable handle 132 can be rotated about the fulcrum pins 133. In this case, the action pins 135 move in the action grooves 120a of the unit body 120 along the axial direction as the movable handle 132 rotates.

The unit body 120 includes a drive mechanism 140 therein. The drive mechanism 140 is located on the perimeter of the probe 110 when the vibrator 10 is mounted on the unit body 120 while the probe 110 is attached to the horn 14. The drive mechanism 140 includes a connection member 141, a pipe fixing member 142, a driving force transmission member 143, a slide support member 144, and a contact member 145.

The connection member 141 is attached to the opening at the distal end of the unit body 120 via a fixing ring 146 so that it can rotate inside the unit body 120 about the axis thereof. As obvious from FIG. 5, the connection member 141 is formed in a cylindrical shape having an outer diameter that increases stepwise toward the proximal end. The connection member 141 has an elliptical hole 141a extending along the axial direction at a portion located closest to the proximal end. A rotary knob 147 for rotating operation is attached to the connection member 141 on the perimeter at a portion protruded from the distal end of the unit body 120.

The pipe fixing member 142 is formed in a cylindrical shape and attached to the inner circumferential surface in the distal end of the connection member 141 via a fixing pin 142a to rotate together with the connection member 141.

The driving force transmission member 143 is located on the inner circumferential surface in the proximal end of the connection member 141, and can slidably move along the axial direction of the connection member 141. The driving force transmission member 143 includes an engaging pin 143a on the outer circumferential surface thereof, and can rotate integrally with the connection member 141 when the engaging pin 143a is engaged in the elliptical hole 141a of the connection member 141. To ensure air-tightness between the outer circumference of the driving force transmission member 143 and the inner circumferential surface of the connection member 141, a packing 143b is mounted on the outer circumference. This packing 143b serves to prevent an aeroperitoneum gas from externally leaking during a surgical operation under laparoscope.

The pipe fixing member 142 and the driving force transmission member 143 are provided with interference preventive rings 142b and 143c, respectively on the inner circumferential surfaces. The interference preventive rings 142b and 143c are mounted on the pipe fixing member 142 and the driving force transmission member 143 for the purpose of preventing the probe 110 from contacting directly with the pipe fixing member 142 or the driving force transmission member 143. A resin having a low friction coefficient such as PTFE is molded to form rings, which are applied as the interference preventive rings 142b and 143c.

The slide support member 144 is formed in a cylindrical shape having a flange-like support 144a at the proximal end thereof. It is coupled to the proximal end of the driving force transmission member 143 via coupling pins 144b. As illustrated in FIG. 6, the proximal end of the slide support member 144 is shaped to have a deformed hole that has flat portions 144c formed at two opposite locations on the inner surface. A slider 148 and a coil spring 149 are arranged on the perimeter of the slide support member 144.

As illustrated in FIG. 5 and FIG. 6, the slider 148 is formed in an annular shape that can fit around the perimeter of the slide support member 144, and can slide along the axial direction of the slide support member 144. The slider 148 has an engaging groove 148a formed in the perimeter thereof. The distal end of the action pin 135 protruded inside the unit body 120 via the action groove 120a engages in the engaging groove 148a.

The coil spring 149 is a compressible spring interposed between the surface on the proximal end of the driving force transmission member 143 and the surface on the distal end of the slider 148. In a normal state, the coil spring 149 moves the slider 148 to a location closest to the proximal end to hold the surface on the proximal end of the slider 148 in contact with the support 144a of the slide support member 144. When the slider 148 moves from this state toward the distal end of the slide support member 144 in the axial direction, a certain spring force acts to press the driving force transmission member 143 toward the distal end.

The contact member 145 is an electrically conductive cylindrical member with a distal end having an external form corresponding to the flat portion 144c of the slide support member 144. The contact member 145 is arranged in such a manner that the distal end fits in the proximal end of the slide support member 144. The contact member 145 is arranged at a location so as to cover the perimeter of the input portion 111 of the probe 110, and has an inner circumferential surface shaped to fit around the flange 115 of the probe 110.

The contact member 145 is provided with elastic pieces 145a on the proximal end thereof. The elastic pieces 145a are configured by forming slits (not shown) in the proximal end of the contact member 145 along the axial direction, each having a protrusion 145b at an individual free end. The protrusion 145b is configured to have an outer diameter larger than the inner diameter of the internal connection member 122. When the protrusion 145b is engaged in the annular groove 122a formed in the inner circumferential surface of the internal connection member 122, the contact member 145 is allowed to rotate relative to the internal connection member 122 and is restricted to move in the axial direction.

A connection rubber 150 molded of an electrically conductive rubber is attached to the distal end of the contact member 145. The connection rubber 150 is employed to ensure an electrical connection with the probe 110 and is press-contacted with the outer circumferential surface of the probe 110 in the vicinity of the position corresponding to the segment of vibration in the probe 110. A protrusion 150a is formed outside the connection rubber 150 to ensure airtightness between the connection rubber 150 and the inner circumferential surface of the slide support member 144. The protrusion 150a of the connection rubber 150 serves to prevent an aeroperitoneum gas from externally leaking during a surgical operation under laparoscope.

The reference numeral 151 in FIG. 5 denotes a high-frequency connection pin provided in the unit body 120. The high-frequency connection pin 151 is connected to an active cord for supplying a high-frequency current from a high-frequency cautery power source (not shown) and is attached to the proximal end of the unit body 120 so as to be electrically connected to the internal connection member 122. An insulating cover 152 is attached to the proximal end of the high-frequency connection pin 151 to ensure the electrical security while the active cord is attached thereto.

In the drive mechanism 140 thus configured, when the rotary knob 147 is rotated, the connection member 141, the pipe fixing member 142, the driving force transmission member 143 and the slide support member 144 follow to rotate relative to the unit body 120. In addition, the slide support member 144 rotates the contact member 145 and the probe 110 in the same direction. Even when the rotary knob 147 rotates, the protrusion 145b of the contact member 145 is always in contact with the internal connection member 122 to maintain electric connection therebetween by the elasticity of the elastic pieces 145a. As a result, regardless of the operation of the rotary knob 147, the probe 110 is always electrically connected with the high-frequency connection pin 151 via the internal connection member 122, the contact member 145, and the connection rubber 150. In this situation, the treatment portion 113 is employed, for example, to flow the high-frequency current to treat a living tissue.

The treatment unit 100 further includes an insertion sheath 160 at the distal end of the unit body 120.

The insertion sheath 160 is an elongated small-diameter portion to be inserted into a hollow portion of the body in a patient during a surgical operation under laparoscope, and has a double structure that includes an outer pipe 161 and an inner pipe 162. The outer pipe 161 extends from the distal end to the inside of the rotary knob 147 and the proximal end thereof is fixed on the inner circumferential surface of the pipe fixing member 142. The outer circumferential surface of the outer pipe 161 is covered by an insulating tube 163. The inner pipe 162 forms a channel inside for passing the waveguide portion 112 and the treatment portion 113 of the probe 110 through. The rubber rings 118 are interposed between the inner pipe 162 and the waveguide portion 112.

Figure 2:
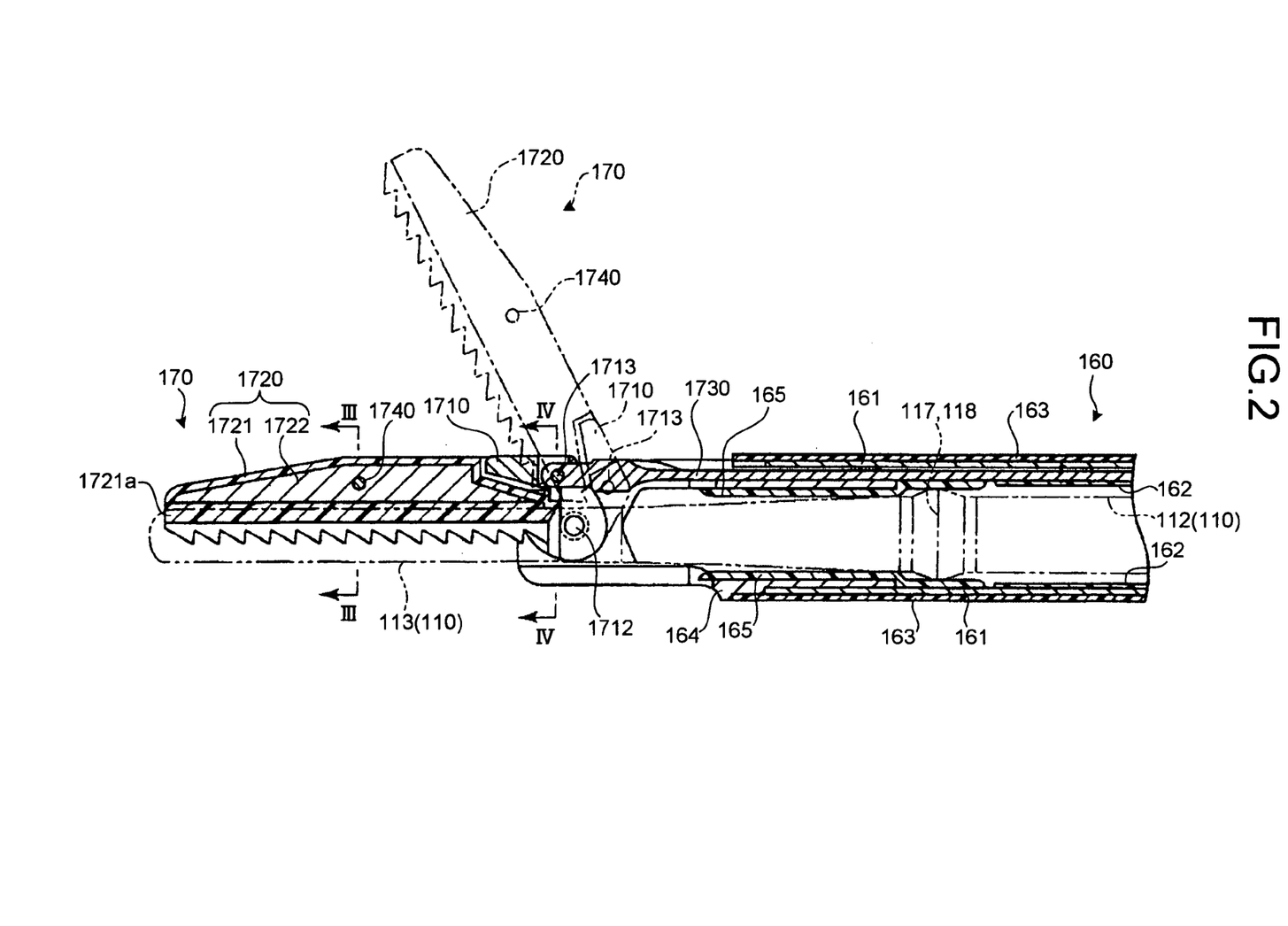
FIG. 2 is a cross-sectional view of a distal end of the ultrasonic treatment apparatus illustrated in FIG. 1.

A tip cover 164 is attached to the distal end of the outer pipe 161 of the insertion sheath 160 as illustrated in FIG. 2. The tip cover 164 is employed to pass the probe 110 through via a retaining member 165, and is arranged at a location that externally exposes the treatment portion 113 of the probe 110 from the distal end of the cover when the vibrator 10 is mounted on the unit body 120 while the horn 14 is attached to the probe 110.

A tip action unit 170 is provided on the tip cover 164. The tip action unit 170 is employed to grasp a living tissue between the section 170 and the treatment portion 113 of the probe 110, and includes a jaw 1710 and a grasping member 1720.

Figure 4:
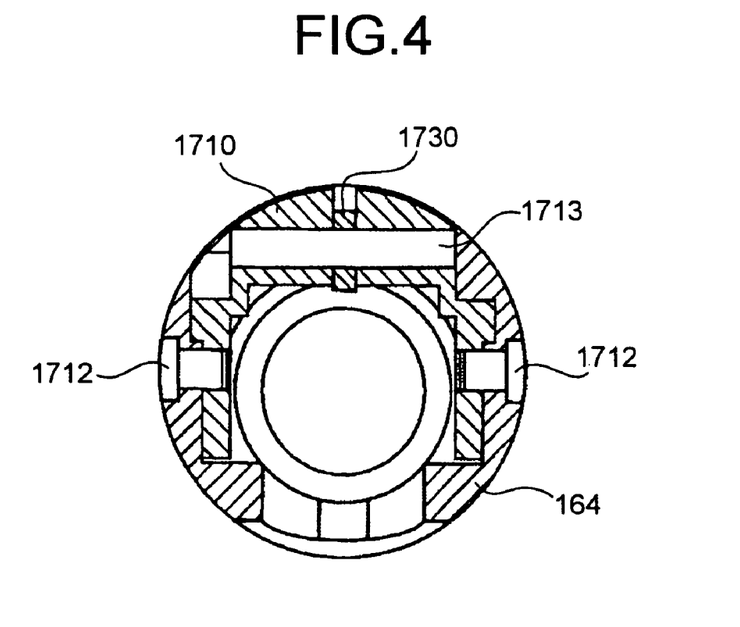
FIG. 4 is a cross-sectional view cut along IV-IV line in FIG. 3.

The jaw 1710 is molded of a metal having bio-compatibility and desired rigidity and tenacity, such as stainless steel. It has bifurcated tip supports 1711 as illustrated in FIG. 8(a) and FIG. 8(b). As illustrated in FIG. 4, the jaw 1710 has a proximal end attached to the tip cover 164 using two rotation support pins 1712 that are arranged laterally on the same axis. The jaw 1710 can rotate about the axis that is orthogonal to the extending direction of the insertion sheath 160.

A link pin 1713 is attached to the jaw 1710. The link pin 1713 is arranged at a location decentered to avoid the rotation support pins 1712 along the axial direction of the rotation support pins 1712 and is connected to a drive link 1730 at the distal end. The drive link 1730 extends within the insertion sheath 160 along the channel provided between the outer pipe 161 and the inner pipe 162. The proximal end of the drive link is coupled to the driving force transmission member 143 via a driving force transmission pin 1731 as illustrated in FIG. 5.

Figure 3:
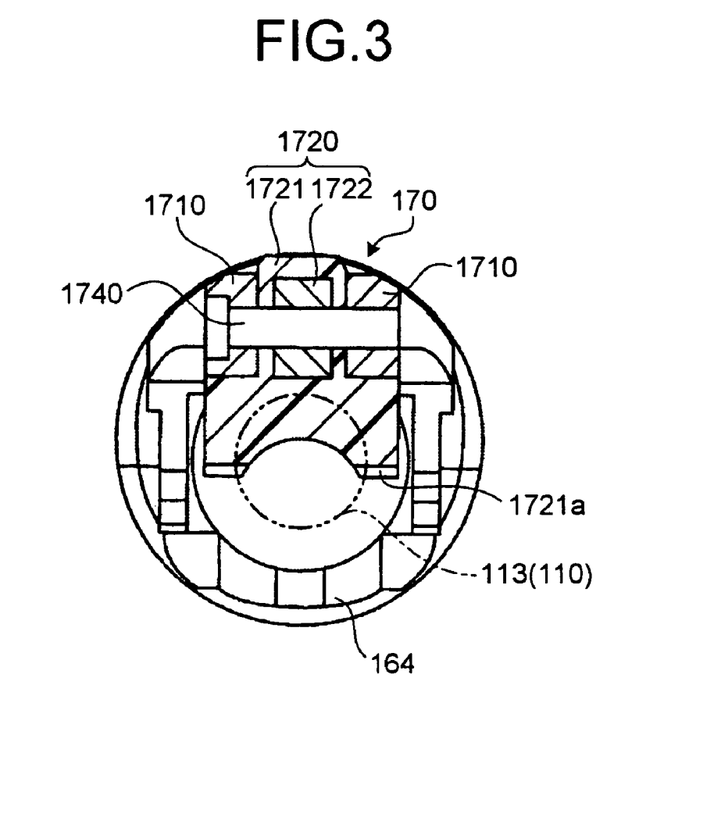
FIG. 3 is a cross-sectional view cut along III-III line in FIG. 2.

The grasping member 1720 is a portion that directly contacts with living tissues such as blood vessels together with the treatment portion 113 of the probe 110. The grasping member 1720 includes a first element 1721 and a second element 1722. The first element 1721 has a pinch 1721a that opposes to the treatment portion 113 of the probe 110, and a tip bearing 1721b that is mounted in between the tip supports 1711 of the jaw 1710. The first element 1721 is integrally molded of a resin, which exhibits a low friction coefficient against the probe 110 and is excellent in heat resistance (about 170° C.) and abrasion resistance, such as PTFE and perfluoroalkoxylalkane (PFA). As illustrated in FIG. 3, the pinch 1721a has a trench with a curved central portion corresponding to the treatment portion 113 of the probe 110, and serrated parts on portions at both sides of the trench. The second element 1722 is molded of a metal having higher rigidity and tenacity compared to PTFE and PFA, such as a stainless steel. The second element 1722 is buried as reinforcement in the first element 1721. The second element 1722 extends almost along the entire length of the first element 1721 and has a portion corresponding to the tip bearing 1721b of the first element 1721. The outer surface of the second element 1722 is covered entirely by the first element 1721 and has no portion which is externally exposed.

The grasping member 1720 is supported pivotably movable about the axis that is orthogonal to the extending direction of the insertion sheath 160. In this case, the tip bearing 1721b is supported in between the tip supports 1711 of the jaw 1710, and a support pin 1740 is passed through the tip supports 1711 and tip bearing 1721b and the second element 1722.

The grasping member 1720 can be produced easily by insert molding the first element 1721 around the second element 1722 if PFA is applied as the first element 1721.

If PTFE is applied as the first element 1721 of the grasping member 1720, a method illustrated in FIG. 9(a) to FIG. 9(c) may be employed. First, as illustrated in FIG. 9(a), the second element 1722 molded in a desired shape and a base 1721A and a lid 1721B both molded of PTFE are prepared. The base 1721A is formed in a rectangular parallelepiped shape sufficient for molding the lower half of the first element 1721. The lid 1721B is formed in a rectangular parallelepiped shape sufficient for molding the upper half of the first element 1721. A recess 1721C is formed in the lid 1721B to accommodate the second element 1722 therein.

Next, the second element 1722 is accommodated in the recess 1721C, and then the base 1721A is joined and thermally welded with the lid 1721B to produce a rough material as illustrated in FIG. 9(b).

Finally, when the rough material produced as illustrated in FIG. 9(b) is dug out, the grasping member 1720 in a desired shape can be obtained as illustrated in FIG. 9(c).

Operation of the ultrasonic treatment apparatus applied to treatment of living tissues will be described below.

To grasp a living tissue, fingers are engaged in the stationary finger-engaging portion 131a and the movable finger-engaging portion 132a and operated to open/close. As a result, the slider 148 engaged with the action pin 135 of the movable handle 132 moves along the axial direction, and the driving force transmission member 143 moves back and forth along the axial direction. The back-and-forth movement of the driving force transmission member 143 causes back-and-forth movement of the drive link 1703, which is transmitted to the jaw 1710. Then, the jaw 1710 rotates about the rotation support pins 1712; and the grasping member 1720 moves in an opening/closing manner relative to the treatment portion 113 of the probe 110. As a result, the treatment portion 113 of the probe 110 and the grasping member 1720 can grasp the living tissue such as a blood vessel therebetween.

In the ultrasonic treatment apparatus, the coil spring 149 is interposed between the driving force transmission member 143 and the slider 148. Therefore, even if any operating force is applied to the movable handle 132, the driving force transmission member 143 can be pressed toward the distal end by the spring force from the coil spring 149 to move the jaw 1710 to a closed position with a certain force. The grasping member 1720 is pivotably movable about the axis of the support pin 1740 relative to the jaw 1710 that is movable in an opening/closing manner in response to the operation of the operating section 130. Accordingly, a uniform grasping force can be applied over the entire length of the living tissue to perform a treatment thereto. Even if the treatment portion 113 of the probe 110 is distorted due to the counteraction on grasping the living tissue, the grasping member 1720 pivotably moves about the axis of the support pin 1740 to follow the distortion of the probe 110. Therefore, the uniform grasping force can be constantly applied to the living tissue.

When the ultrasonic vibrator 12 of the vibrator 10 is operated to vibrate after the living tissue is grasped, the treatment portion 113 of the probe 110 starts an ultrasonic vibration. As a result, a treatment such as coagulation and cutting can be performed to the living tissue such as the blood vessel while constantly applying the uniform grasping force thereto.

In the ultrasonic treatment apparatus, the reinforcing second element 1722 of the grasping member 1720 is entirely buried in the first element 1721 to achieve a simple external form with no gaps present between the first element 1721 and the second element 1722. Therefore, it is possible to easily perform reliable cleaning in a short time even if contaminants such as blood are attached. As a result, the treatment unit 100 of the ultrasonic treatment apparatus can be reused readily, which contributes to reduction of environmental burden and surgical operation expenses.

The shapes of the jaw 1710 and the grasping member 1720 in the tip action unit 170 are not limited to those described in the first embodiment. For example, they may be shaped in extended curves. While the second element 1722 includes the portion pivotably supported by the jaw 1710 in the grasping member 1720, the second element 1722 is not required to include such the portion pivotably supported by the jaw 1710. In another application, the grasping member 1720 may consist only of the first element 1721 with no need for the second element 1722.

Second Embodiment

FIG. 10 to FIG. 14 are schematic diagrams for illustrating an ultrasonic treatment apparatus with application of an ultrasonic treatment apparatus according to a second embodiment of the present invention. As is the ultrasonic treatment apparatus described in the first embodiment, the ultrasonic treatment apparatus herein disclosed is employed for performing treatments such as cutting, removing, and coagulation of living tissues using ultrasonic waves. The configuration of a grasping member at a tip action unit is the only difference between the ultrasonic treatment apparatus herein and the apparatus according to the first embodiment.

Figure 10:
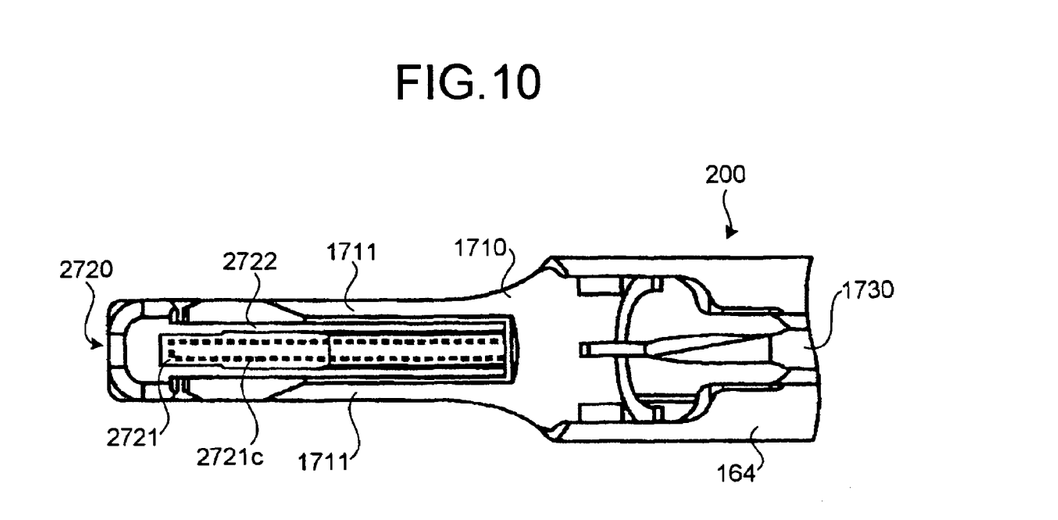
FIG. 10 is a plan view of an ultrasonic treatment apparatus according to a second embodiment of the present invention.
Figure 11:
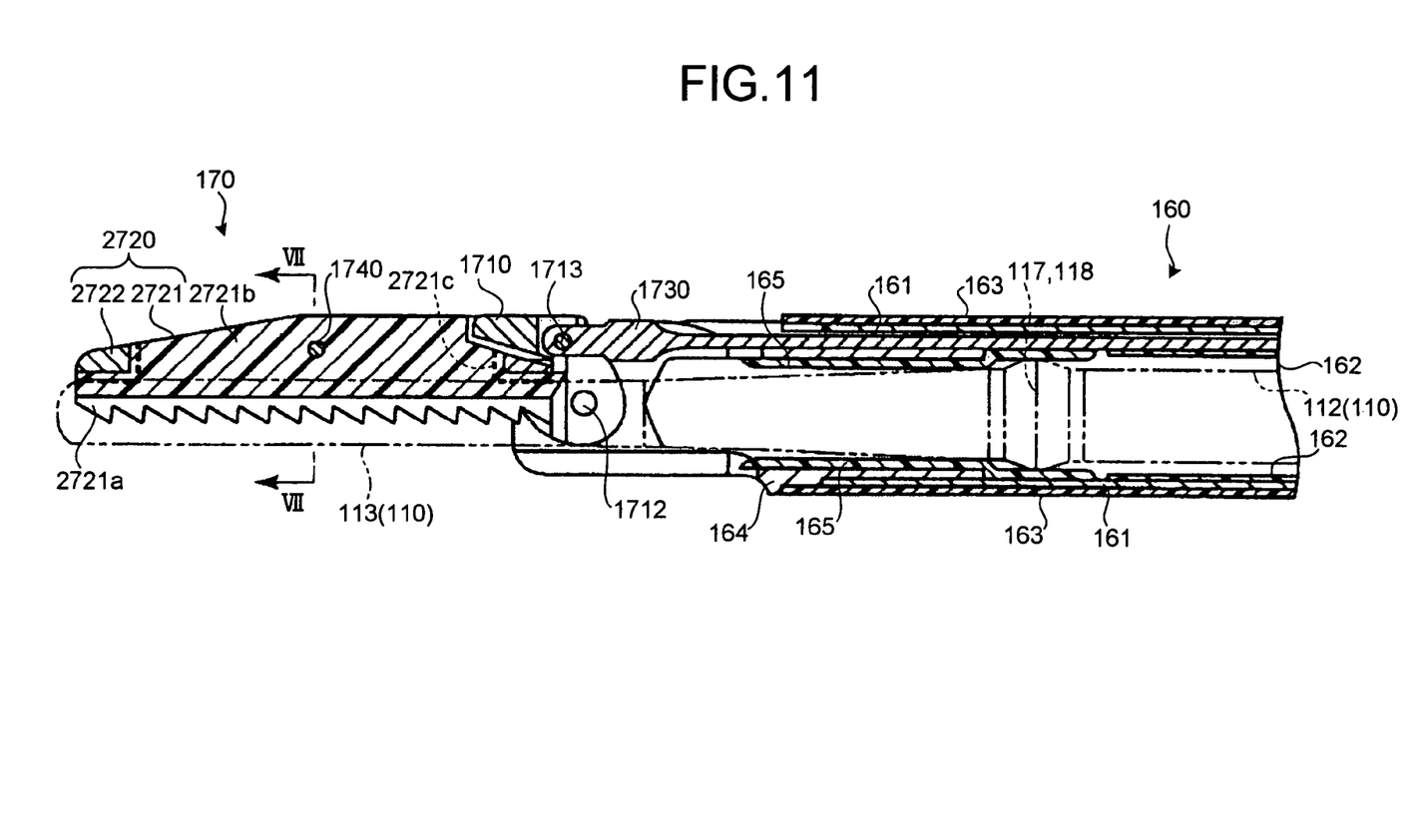
FIG. 11 is a cross-sectional side view of the ultrasonic treatment apparatus illustrated in FIG. 10.
Figure 12:
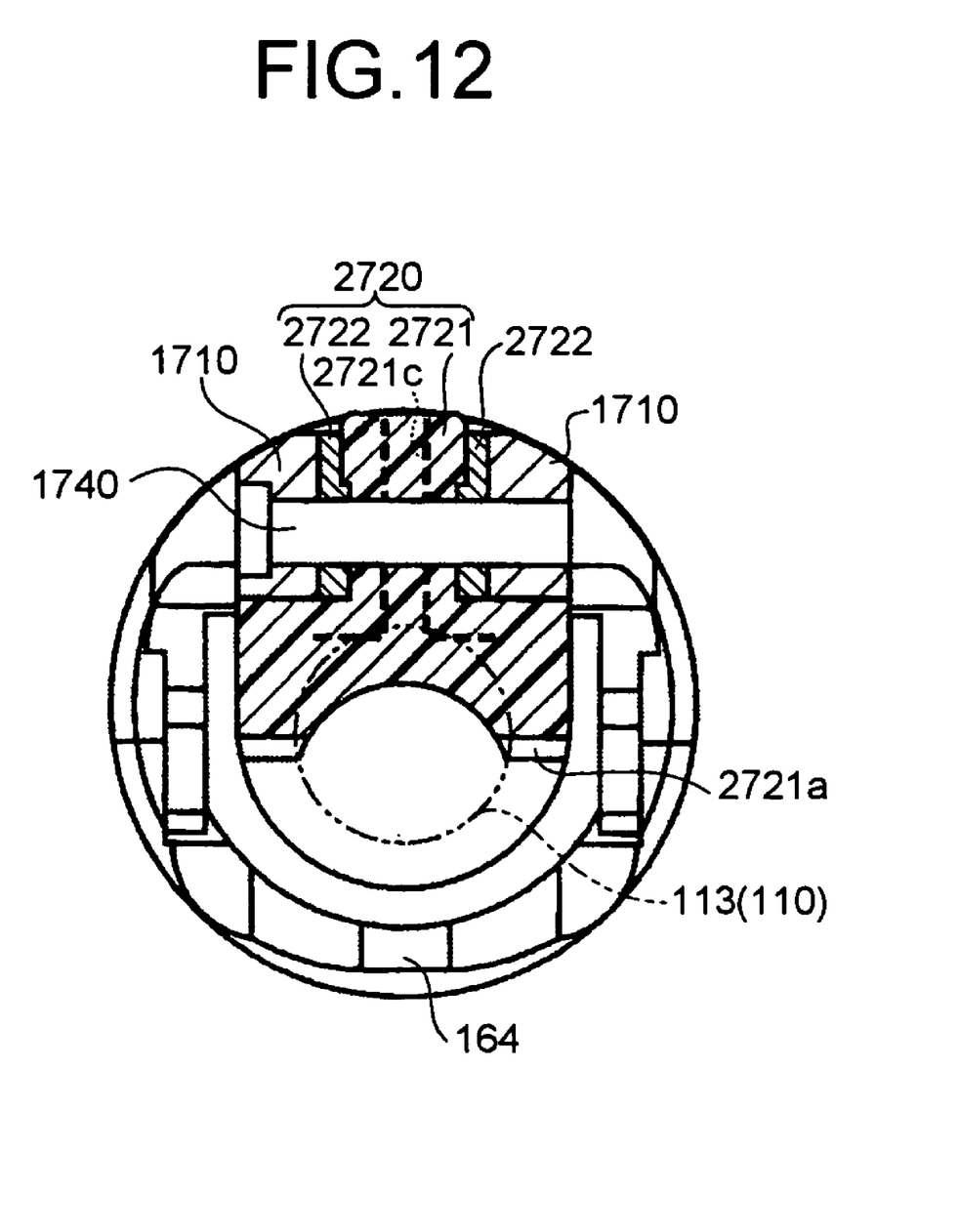
FIG. 12 is a cross-sectional view cut along XII-XII line in FIG. 11.
Figure 13:
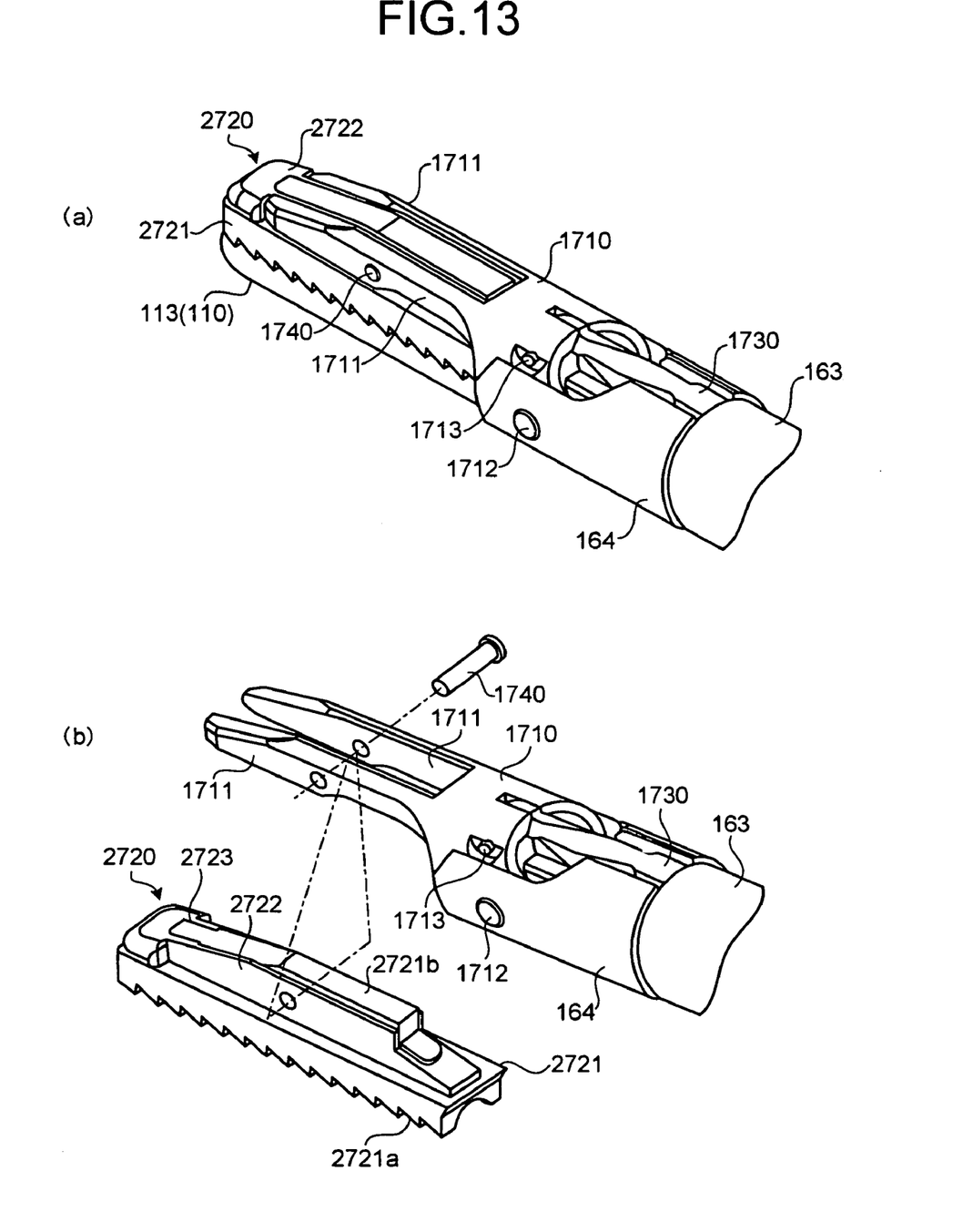
FIG. 13(a) is a perspective view of the tip action unit.
FIG. 13(b) is an exploded perspective view of the tip action unit.

In a grasping member 2720 applied to a treatment unit 200 of the second embodiment, a second element 2722 molded of a metal is arranged in an exposed manner on the outer surface of a first element 2721 molded of PTFE or PFA. The first element 2721 has a pinch 2721a that opposes to the treatment portion 113 of the probe 110, and a tip bearing 2721b that is mounted in between the tip supports 1711 of the jaw 1710. As illustrated in FIG. 10 to FIG. 12 with bold dashed lines, a coloring marker 2721c is embedded in a peripheral thick region of the first element 2721. The coloring marker 2721c appears outward to notify of a usable limit when the first element 2721 wears away. The second element 2722 is arranged on both sides of the tip bearing 2721b of the first element 2721 and extends almost along the entire length of the first element 1721.

As for configurations identical to those of the first embodiment, like reference numerals are designated and descriptions thereof are omitted.

The grasping member 2720 is supported pivotably movable about the axis that is orthogonal to the extending direction of the insertion sheath 160 as illustrated in FIG. 13(a) and FIG. 13(b). In this case, the tip bearing 2721b of the first element 2721 and the second element 2722 are supported in between the tip supports 1711 of the jaw 1710, and the support pin 1740 is passed through the tip supports 1711, the second element 2722, and the tip bearing 2721b.

The grasping member 2720 in the second embodiment may be produced by outsert molding the first element 2721 inside the second element 2722 if PFA is applied as the first element 2721. In this case, on the outsert molding of the first element 2721, the first element 2721 is intimately contacted with the second element 2722, remaining no gaps between both.

Figure 14:
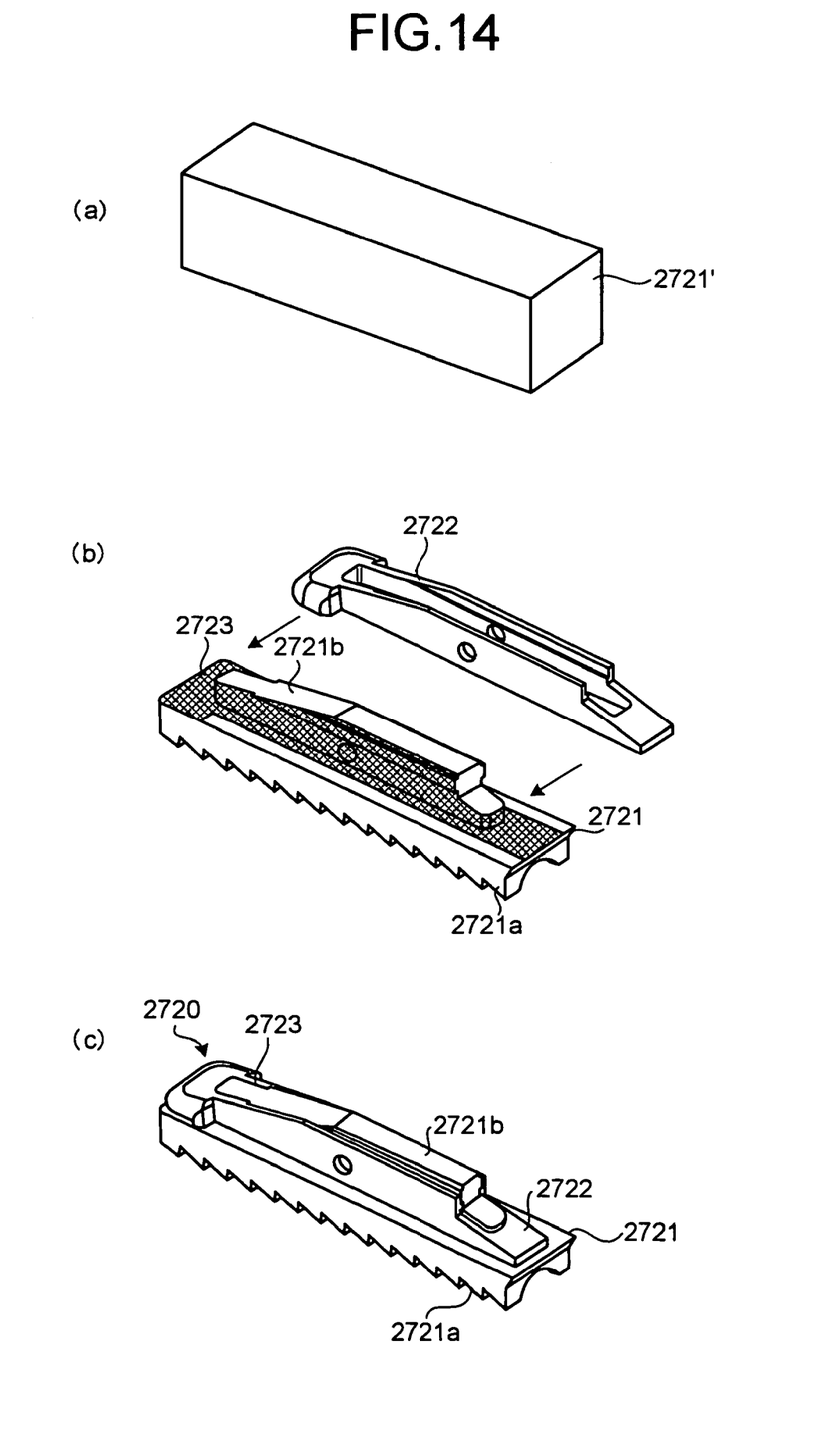
FIG. 14(a) to FIG. 14(c) are schematic diagrams for illustrating process steps of manufacturing the grasping member.

If PTFE is applied as the first element 2721 of the grasping member 2720, a method illustrated in FIG. 14(*a*) to FIG. 14(*c*) may be employed because the first element 2721 is hardly subjected to outsert molding.

First, as illustrated in FIG. 14(*a*), a shape of the first element 2721 is cut out of a rectangular parallelepiped material 2721' composed of PTFE.

If the second element 2722 is simply disposed on the first element 2721 thus cut out, gaps may be possibly defined between both. Therefore, as illustrated in FIG. 14(*b*), the surface of a portion of the first element 2721 that is employed to arrange the second element 2722 thereon is roughened chemically or physically. Thereafter, an adhesive 2723 (a crosshatched portion in FIG. 14(*b*)) is applied as filler between the first element 2721 and the second element 2722, and the second element 2722 is disposed thereon. The adhesive 2723 may be composed of any one of silicones, rubbers, resins, and the like, preferably one having heat resistance and having resistance against sterilization.

Finally, protruded parts of the adhesive 2723 are cut off to finish the second element 2722 having a desired shape as illustrated in FIG. 14(*c*). Preferably, the adhesive 2723 is such that the exposed portion connected to the outer surfaces of the first element 2721 and the second element 2722 form no step therebetween. The coloring marker 2721*c* may be embedded in the first element 2721 by filling the adhesive 2723.

The above process steps enable the filler or adhesive to contact the first element 2721 intimately with the second element 2722 without formation of any gap between both contained in the grasping member 2720.

Also in the ultrasonic treatment apparatus with application of the grasping member 2720 thus configured, the coil spring 149 is interposed between the driving force transmission member 143 and the slider 148. Therefore, even if any operating force is applied to the movable handle 132, the driving force transmission member 143 can be pressed toward the distal end by the spring force from the coil spring 149 to move the jaw 1710 to a closed position with a certain force. The grasping member 2720 is pivotably movable about the axis of the support pin 1740 relative to the jaw 1710 that is movable in an opening/closing manner in response to the operation of the operating section 130. Accordingly, a uniform grasping force can be applied over the entire length of the living tissue to perform a treatment thereto. Even if the treatment portion 113 of the probe 110 is distorted due to the counteraction on grasping the living tissue, the grasping member 2720 pivotably moves about the axis of the support pin 1740 to follow the distortion of the probe 110. Therefore, the uniform grasping force can be constantly applied to the living tissue.

When the ultrasonic vibrator 12 of the vibrator 10 is operated to vibrate after the living tissue is grasped, the treatment portion 113 of the probe 110 starts an ultrasonic vibration. As a result, a treatment such as coagulation and cutting can be performed to the living tissue such as the blood vessel while constantly applying the uniform grasping force thereto.

In the ultrasonic treatment apparatus, the first element 2721 can be intimately contacted with the second element 2722 of the grasping member 2720 so as not to form any gap therebetween even though they are molded by any one of the above methods. Therefore, it is possible to easily perform reliable cleaning in a short time even if contaminants such as blood are attached. As a result, the ultrasonic treatment apparatus can be reused readily, which contributes to reduction of environmental burden and surgical operation expenses.

The shapes of the jaw 1710 and the grasping member 2720 in the tip action unit 170 are not limited to those described in the first embodiment. For example, they may be shaped in extended curves. While the second element 2722 includes the portion pivotably supported by the jaw 1710 in the grasping member 2720, the second element 2722 is not required to include such the portion pivotably supported by the jaw 1710. Although the adhesive 2723 having the adhesive function is applied as the filler, it is not always required to employ one having the adhesive function.

INDUSTRIAL APPLICABILITY

As described above, the present invention is suitable for performing a desired medical treatment of a living tissue. The ultrasonic treatment apparatus includes an ultrasonic-vibrating probe, and a tip action unit that moves in an opening/closing manner with respect to the probe on operation of an operating section. An ultrasonic vibration is applied to the probe while grasping the living tissue between the probe and the tip action unit.

The invention claimed is:

1. An ultrasonic treatment apparatus for performing a medical treatment to a living tissue, comprising:
   a probe to which ultrasonic vibration is applied; and
   a tip action unit that moves in an opening/closing manner with respect to the probe on operation of an operating section, wherein
   the tip action unit includes
      a jaw that moves in an opening/closing manner in response to the operation of the operating section; and
      a grasping member pivotably supported by the jaw for grasping the living tissue with the probe,
   the grasping member includes
      a body element molded of a heat resistant resin; and
      a reinforcement member embedded in the body element, and
   the ultrasonic vibration is applied to the probe while grasping the living tissue between the probe and the tip action unit.

2. The ultrasonic treatment apparatus according to claim 1, wherein the reinforcement member is made of a metallic material extended along an extending direction of the probe.

3. The ultrasonic treatment apparatus according to claim 1, wherein the reinforcement member includes a portion pivotably supported by the jaw.

4. An ultrasonic treatment apparatus for performing a medical treatment to a living tissue, comprising:
   a probe to which ultrasonic vibration is applied; and
   a tip action unit that moves in an opening/closing manner with respect to the probe on operation of an operating section, wherein
   the tip action unit includes
      a jaw that moves in an opening/closing manner in response to the operation of the operating section; and
      a grasping member pivotably supported by the jaw for grasping the living tissue with the probe,
      the grasping member includes a body element molded of a heat resistant resin; and a reinforcement member fitted with the body element to cover a portion of the body element, and a filling member is filled between the body element and the reinforcement member to tightly contact the body element with the reinforcement member; and the ultrasonic vibration is applied to the probe while grasping the living tissue between the probe and the tip action unit.

5. The ultrasonic treatment apparatus according to claim 4, wherein the reinforcement member is made of a metallic material extended along an extending direction of the probe.

6. The ultrasonic treatment apparatus according to claim 4, wherein the reinforcement member includes a portion pivotably supported by the jaw.

* * * * *